United States Patent [19]

Ahr

[11] Patent Number: 4,826,499

[45] Date of Patent: May 2, 1989

[54] ABSORBENT GARMENT HAVING LATERALLY DISPLACEABLE FASTENING MEANS

[75] Inventor: Nicholas A. Ahr, Cincinnati, Ohio

[73] Assignee: The Proctor & Gamble Company, Cincinnati, Ohio

[21] Appl. No.: 62,527

[22] Filed: Jun. 12, 1987

[51] Int. Cl.⁴ .................................................. A41B 13/02
[52] U.S. Cl. ..................................... 604/389; 604/385.2
[58] Field of Search ................. 604/385.1, 385.2, 389, 604/390

[56] References Cited

U.S. PATENT DOCUMENTS

| | | | |
|---|---|---|---|
| 3,800,796 | 4/1974 | Jacob | 128/284 |
| 3,920,018 | 11/1975 | Schaar | 128/287 |
| 3,951,150 | 4/1976 | Schaar | 128/287 |
| 3,987,794 | 10/1976 | Schaar | 128/287 |
| 3,990,450 | 11/1976 | Schaar | 128/287 |
| 4,014,338 | 3/1977 | Schaar | 128/287 |
| 4,036,233 | 7/1977 | Kozak | 128/287 |
| 4,066,081 | 1/1978 | Schaar | 128/287 |
| 4,074,716 | 2/1978 | Schaar | 128/287 |
| 4,090,516 | 5/1978 | Schaar | 128/287 |
| 4,158,363 | 6/1979 | Schaar | 128/287 |
| 4,182,334 | 1/1980 | Johnson | 604/393 X |
| 4,209,016 | 6/1980 | Schaar | 128/287 |
| 4,210,143 | 7/1980 | de Jonckheere | 604/389 |
| 4,381,781 | 5/1983 | Sciaraffa et al. | 604/372 |
| 4,389,212 | 6/1983 | Tritsch | 604/389 |
| 4,522,853 | 6/1985 | Szonn et al. | 428/40 |
| 4,643,729 | 2/1987 | LaPlanche | 604/389 |

Primary Examiner—Samuel Scott
Assistant Examiner—Allen J. Flanigan
Attorney, Agent, or Firm—Larry L. Huston; John M. Pollaro; Frederick H. Braun

[57] ABSTRACT

An integral disposable absorbent garment, such as a disposable diaper or an incontinent brief, having a chassis means and an improved fastening system in a waist portion of the chassis means. The fastening system comprises a laterally displaceable elastic member, which is affixed to the chassis means, and a fastening means, such as a refastenable tape, joined to said elastic member. Thus, the fastening means, rather than being affixed to the garment in a fixed relation, is instead laterally displaceable in relation to the balance of the garment. The improved fastening system provides the garment with a better fit, improved adjustability, and the capability of being able to be pulled on or off the wearer without unfastening.

8 Claims, 2 Drawing Sheets

ABSORBENT GARMENT HAVING LATERALLY DISPLACEABLE FASTENING MEANS

FIELD OF THE INVENTION

The present invention relates to disposable absorbent garments such as disposable diapers, and more particularly, to disposable diapers having a laterally displaceable elastic member in the waist portion to which diaper fastening means are attached. The result is a garment having a laterally displaceable fastening means.

BACKGROUND OF THE INVENTION

The major function of absorbent garments such as disposable diapers is to absorb and contain body exudates. Such articles are thus intended to prevent body exudates from soiling, wetting, or otherwise contaminating clothing or other articles, such as bedding, that come in contact with the wearer. In general, disposable diapers all have the same basic structure which comprises a liquid permeable topsheet, a liquid impermeable backsheet, an absorbent core positioned between said topsheet and said backsheet, and a means for fastening the diaper about the wearer's waist.

The prior art teaches numerous variations of fastening systems. In order to try to improve the fit of the diaper, a number of ways have been attempted to provide elastic fastening systems in the diaper. For example, U.S. Pat. No. 3,800,796, which issued to Jacob on Apr. 2, 1974, teaches an elastic strip fastener tab which provides as diaper with an elastically extensible side waistband, Other techinques for providing elastic characteristics in tape tabs are disclosed in U.S. Pat. Nos. 4,209,016, which issued to Schaar on June 24, 1980; 4,158,363, which issued to Schaar on June 19, 1979; 4,090,516, which issued to Schaar on May 23, 1978; 4,074,716, which issued to Schaar on Feb. 21, 1978; 4,006,081 which issued to Schaar on Jan. 3, 1978; and 4,389,212, which issued to Tritsch on June 21, 1983.

A technique for providing a diaper with a stretchable waistband so as to improve fit is disclosed in U.S. Pat. No. 4,036,233, which issued to Kozak on July 19, 1977, and which teaches a diaper fabricated from a stretchable material which is bonded to a non-stretchable material, wherein openings are provided in the waistband area of the non-stretchable material to permit stretching of the stretchable material. Fastening tapes are then attached to the stretchable waistband. Still another technique for providing a diaper with a stretchable waistband so as to improve fit is disclosed in U.S. Pat. No. 4,014,338, which issued to Schaar on Mar. 29, 1977, and which teaches a pleated diaper having an elastic member in a waistline portion thereof, to which fastening means are attached.

While the fastening systems discussed above do provide some measure of improvement over the more common non-elastic fastening systems, the devices fail to adequately address the need for a cost-effective fastening system which provides the garment with a better fit, improved adjustability, and the capability of being able to be pulled on or off the wearer without unfastening.

Therefore, it is an object of the present invention to provide an absorbent garment having an improved fastening system. It is an additional object of the present invention to provide an absorbent garment having a fastening means which is laterally displaceable in relation to the balance of the garment. It is an additional object of the present invention to provide an absorbent garment having a laterally displaceable elastic member in a waist portion thereof to which diaper fastening means are attached, thus resulting in a fastening means which is laterally displaceable.

These and other objects of the present invention will be more readily apparent when considered in reference to the following description and when taken in conjunction with the accompanying drawings.

SUMMARY OF THE INVENTION

In accordance with the present invention, an integral disposable absorbent garment, such as a diaper, is provided with a chassis means and a laterally displaceable fastening system in a waist portion of the garment. The chassis means preferably comprises an absorbent core having a garment surface and a body surface, a liquid impervious backsheet positioned adjacent the garment surface of the absorbent core, and a liquid pervious topsheet positioned adjacent the body surface of the absorbent core. The fastening system comprises a laterally displaceable elastic member and a fastening means joined to said elastic member. Thus, the fastening means, rather than being affixed to the garment in a fixed relation, is instead laterally displaceable in relation to the balance of the garment.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements and in which:

DETAILED DECRIPTION OF THE PREFERRED EMBODIMENTS

The present invention relates to integral disposable absorbent garments such as disposable diapers, and more particularly, to integral disposable absorbent garments having an improved fastening system.

Figure 1:
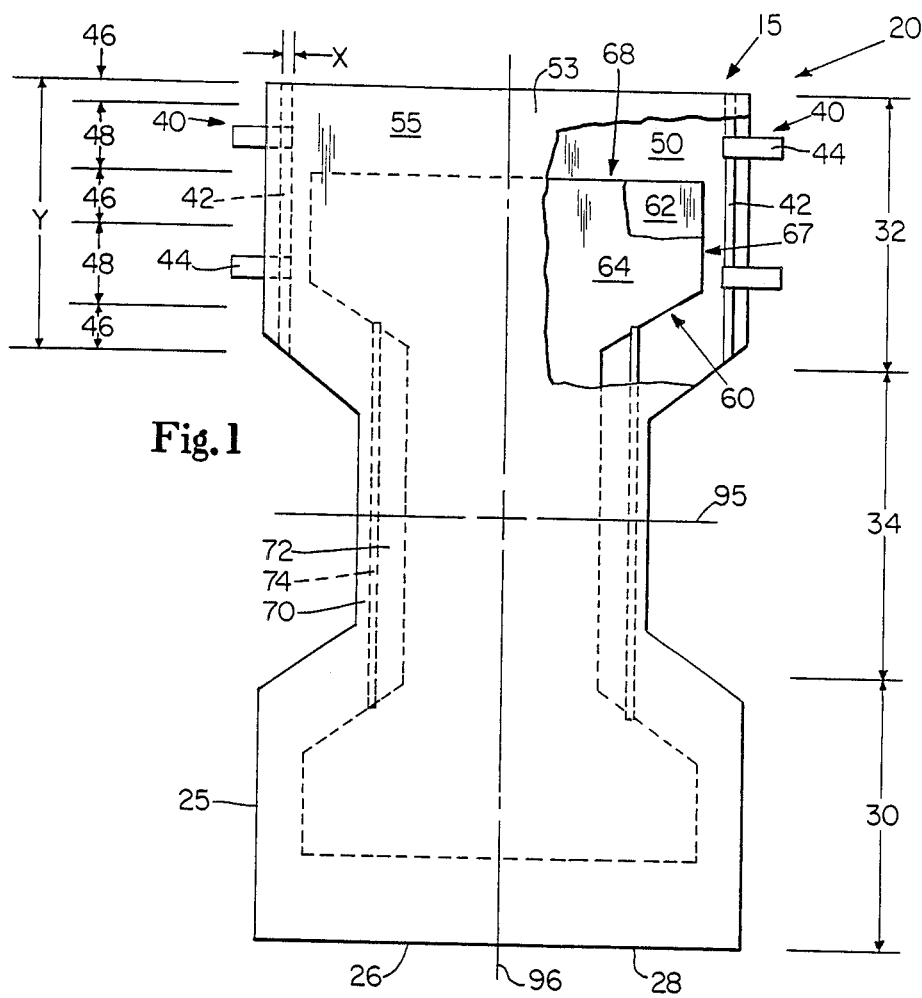
FIG. 1 is a plan view of a disposable diaper embodiment of the present invention having portions cut away to reveal underlying structure.

As used herein, the term "integral disposable absorbent garment" refers to articles which absorb and contain body exudates and more specifically refers to garments which are placed against or in proximity to the body of a wearer to absorb and contain the various exudates discharged from the body and which are intended to be discarded after a single use (i.e., they are not intended to be laundered or otherwise restored or reused), and which do not require separate manipulative parts like a separate holder and liner. A preferred embodiment of the integral disposable absorbent garment of the present invention is shown in FIG. 1 as it would be used in a diaper 20. As used herein, the term "diaper" refers to a garment generally worn by infants or incontinent persons about the lower torso.

FIG. 1 is a partially cut away plan view of the diaper 20 of the present invention in its flat out, uncontracted state (i.e., with all elastic induced contraction pulled out) with portions of the structure being cut-away to more clearly show the construction of the diaper 20 and with the portion of the diaper 20 which contacts the wearer facing the viewer. As can be seen in FIG. 1, the diaper 20 basically comprises a chassis means 15 and an improved fastening system 40. The chassis means 15 may be any means which is generally compressible, conformable, non-irritating to the wearer's skin, and capable of absorbing and containing body exudates, such as feces, urine, blood, pus, and the like. The chassis means 15 has longitudinal edges 25 and end edges 26. In the preferred embodiment shown in FIG. 1, the chassis means 15 comprises a liquid pervious topsheet 55; a liquid impervious backsheet 50; and an absorbent core 60 positioned between said topsheet 55 and said backsheet 50. The absorbent core 60 has core side edges 67 and core waist edges 68.

The improved fastening system 40 comprises a laterally displaceable elastic member 42 and a fastening means 44 joined to said elastic member 42. The elastic member 42 is affixed to the chassis means 15. As used herein, and throughout this specification, the term "affixed" encompasses configurations whereby a first member is directly joined to a second member by affixing the first member directly to the second member and configurations whereby the first member is indirectly joined to the second member by affixing the first member to intermediate members which in turn are affixed to the second member. Specifically, with reference to the elastic member 42 being affixed to the chassis means 15, the term "affixed" encompasses configuration wherein the chassis means 15 comprises only one member and the elastic member 42 is directly or indirectly joined to the chassis means 15 and configurations wherein the chassis means 15 comprises more than one member and the elastic member 42 is directly or indirectly joined to at least one member of the chassis means 15. Because the elastic member 42 is laterally displaceable and because the fastening means 44 is joined to the elastic member 42, the fastening means 44 is laterally displaceable. As used herein, the term "laterally displaceable" refers to the capability of being able to move in a direction generally parallel to the lateral centerline 95 of the diaper 20 when the diaper 20 is in its flat out, uncontracted state, as shown in FIG. 1, while the chassis means 15 remains fixed. As used herein, the term "elastic member" refers to any member having the tendency when strained by stretching, pulling, pushing, or elongating to resist the strain and return to its natural or near natural unstrained state. The term "fastening means" is intended to include any means for fastening, attaching, or affixing one part of the diaper 20 to another part for the purpose of holding or suspending the diaper 20 about the waist of the wearer.

The chassis means 15 has a liquid receiving top surface 53 which is generally defined by the topsheet 55 and a back surface 54 which is generally defined by the backsheet 50. Preferably, the topsheet 55 and the backsheet 50 have length and width dimensions generally larger than the absorbent core 60, so that they extend beyond the core side edges 67 and the core waist edges 68 of the absorbent core 60 where they are associated together in a suitable manner. In the preferred embodiment shown in FIG. 1, the extension of the topsheet 55 and/or the backsheet 50 beyond the core side edges 67 and the core waist edges 68 of the absorbent core 60 forms the longitudinal edges 25 and the end edges 26, respectively, of the diaper 20. The longitudinal edges 25 and the end edges 26 of the diaper 20 comprise the periphery 28 of the diaper 20.

Examining some of the elements of the diaper 20 in more detail, the top sheet 55 is positioned adjacent the body surface 66 of the absorbent core 60 and overlays a major portion of the absorbent core 60 so that when exudates are discharged onto the topsheet 55 they penetrate through the topsheet 55 where they are absorbed by the absorbent core 60. The topsheet 55 is compliant, soft feeling, and non-irrating to the wearer's skin. Further, the topsheet 55 is liquid pervious, permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of hydrophobic material to isolate the wearer's skin from liquids in the absorbent core 60. A particularly preferred topsheet 55 comprises staple length polypropylene fibers having a denier of about 1.5, such as Hercules Type 151 polypropylene, marketed by Hercules, Inc. of Wilmington, Del. As used herein, the term "staple length fibers" refers to those fibers having a length of at least about 15.9 mm (0.625 inches).

There are a number of manufacturing techniques which may be used to manufacture the topsheet 55. For example, the topsheet 55 may be woven, non-woven, spunbonded, carded, or the like. A preferred topsheet 55 is carded and thermally bonded by means well known to those skilled in the fabrics art. Preferably, the topsheet 55 has a weight of from about 18 to about 25 grams per square meter, a minimum dry tensile strength of at least about 400 grams per centimeter in the machine direction and a wet tensile strength of at least about 55 grams per centimeter in the cross-machine direction.

The absorbent core 60 may be any means which is generally compressible, conformable, non-irritating to the wearer's skin and capable of absorbing and containing liquids and certain body exudates. A preferred absorbent core 60 has a body surface 66 and a garment surface 67 and comprises an absorbent layer 62 and first and second tissue layers 64 and 65, respectively. The first and second tissue layers 64 and 65 overlay the major surfaces of the absorbent layer 62 to form the body surface 66 and the garment surface 67 of the absorbent core 60.

The absorbent layer 62 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, absorbent gelling materials, or any equivalent of the absorbent layer 62 should, however, be compatible with the design exudate loading in the intended use of the diaper 20. Further, the size and absorbent capacity of the absorbent layer 62 may be varied to accommodate wearers ranging from infants to adults.

A preferred embodiment of the diaper 20 has an hourglass shaped absorbent layer 62 and is intended to be worn by adults. The absorbent layer 62 is preferably a batt of airfelt about 41.25 cenitmeters (16.5 inches) wide (lateral dimension along the core waist edges 68), about 60 centimeters (24.0 inches) long (longitudinal dimension) and about 15.0 centimeters (6.0 inches) across (lateral dimension) the narrowest part of the crotch region 34. The airfelt used in the absorbent layer 62 has a generally uniform caliper of about 1.0 centimeters (0.40 inch), an absorbent capacity of from about 8 grams to about 16 grams of water per gram of absorbent material, and a weight of from about 0.03 grams per cubic centimeter to about 0.07 grams per cubic centimeter. It should be understood, however, that the size, shape, configuration, and total absorbent capacity of the absorbent layer 62 may be varied to accommodate wearers ranging from infants through adults. Therefore, the dimensions, shape, and configuration of the absorbent layer 62 may be varied (e.g., the absorbent layer 62 may be a varying caliper, or a hydrophilic gradient, or may contain absorbent gelling materials).

The first and second tissue layers 64 and 65 improve the tensile strength of the absorbent core 60 and reduce the tendency of the absorbent layer 62 to split, lump or ball when wetted. The first and second tissue layers 64 and 65 also help to improve lateral wicking of the absorbed exudates, thereby providing a more even distribution of the exudates throughout the absorbent layer 62. While a number of materials and manufacturing techniques may be used to manufacture the first and second tissue layers 64 and 65, satisfactory results have been obtained with sheets of tissue paper having a basis weight of about 16 grams per square meter (10 lbs. per 3,000 square feet) and having an air permeability of about 30.5 cubic meters per minute per square meter (100 cubic feet per minute per square foot) at a pressure differential of about 12.8 millimeters of water (0.5 inch). While the first and second tissue layers 64 and 65 are preferably coterminous with the absorbent layer 62, they may have different dimensions, a different configuration, or they may be omitted entirely.

The backsheet 50 is positioned adjacent the garment surface 67 of the absorbent core 60 and is preferably attached thereto by attachment means (not shown) such as those well known in the art. For example, the backsheet 50 may be secured to the absorbent core 60 by a uniform continuous layer of adhesive, a patterned layer of adhesive, or an array of separate lines or spots of adhesive. Adhesives which have been found to be satisfactory are manufactured by Eastman Chemical Products Company of Kingsport, Tenn., and marketed under the tradename Eastobond A-3 and by Century Adhesives, Inc., of Columbus, Ohio, and marketed under the tradename Century 5227.

The backsheet 50 is impervious to liquids and is preferably manufactured from a thin plastic film, although other flexible liquid impervious materials may also be used. The backsheet 50 prevents the exudates absorbed and contained in the absorbent core 60 from wetting articles which contact the diaper 20 such as bedsheets and undergarments. Preferably, the backsheet 50 is a polyethylene film having a thickness of from about 0.012 m (0.5 mil) to about 0.051 mm (2.0 mils) although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 50 is preferably embossed and/or matte finished to provide a more clothlike appearance. Further, the backsheet 50 may permit vapors to escape from the absorbent core 60 while still preventing exudates from passing through the backsheet 50.

The size of the backsheet 50 and/or the topsheet 55 are dictated by the size of the absorbent core 60 and the exact diaper design selected. In a preferred embodiment, the backsheet 50 and the topsheet 55 have a rectangular shape and extend beyond the absorbent core 60 a minimum distance of at least about 1.3 centimeters to about 2.5 centimeters (about 0.5 to about 1.0 inch) where they are joined directly to each other in the longitudinal edges 25 of the diaper 20 by attachment means (not shown) as are well known in the art. The attachment means may be, for example, a uniform continuous layer of adhesive, a patterned layer of adhesive, or an array of separate lines or spots of adhesive.

Figure 2:
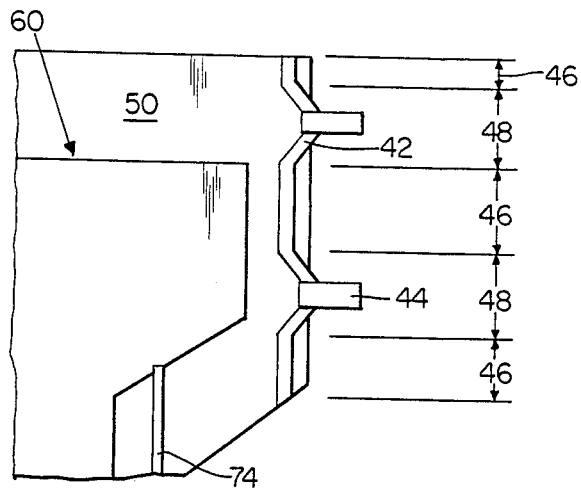
FIG. 2 is a partial plan view of the disposable diaper embodiment of FIG. 1 with the topsheet cut away and showing the present invention in use.

In the preferred embodiment shown in FIG. 1, a pair of fastening systems 40 are positioned in the back waist region 32 of the diaper 20, between the topsheet 55 and the backsheet 50. Each fastening system 40 comprises a laterally displaceable elastic member 42 and a fastening means 44 joined to said elastic member 42. In a preferred embodiment, the elasitc members 42 are elongated rectangular strands of elastic which are longitudinally positioned along each longitudinal edge 25 of the diaper 20 in the back waist region 32. As used herein, the term "longitudinally positioned" is intended to include embodiments wherein the elastic member 42 is positioned such that its major dimension is generally parallel to the longitudinal centerline 96 of the diaper 20, and also, embodiments wherein the elastic member 42 has no single major dimension (i.e., the major and minor dimensions are equal). The "major dimension" is determined as follows: the diaper 20 is laid flat-out as shown in FIG. 1, the elastic member 42 is then measured from its left outermost extremity to its right outermost extremity in a direction parallel to the lateral centerline 95, this is the elastic member's 42 "X" dimension, next, the elastic member 42 is measured from its lower most extremity to its uppermost extremity in a direction parallel to the longitudinal centerline 96, this is the elastic member's 42 "Y" dimension, whichever dimension is greatest, "X" or "Y", is the major dimension. In FIGS. 1, 2, and 5, dimension "Y" is greater than dimension "X" and is, therefore, the major dimension. "X" is the minor dimension. Since the major dimensions are parallel to the longitudinal centerline 96, the elastic members 42 are longitudinally positioned. Conversely, in FIGS. 3 and 4, the dimension "X" is greater than the dimension "Y" and is, therefore, the major dimension. "Y" is the minor dimension. Since the major dimensions are parallel to the lateral centerline 95, the elastic members 42 are laterally positioned. As used herein, the term "laterally positioned" is intended to include embodiments wherein the elastic member is positioned such that its major dimension is generally parallel to the lateral centerline 95 of the diaper 20.

In the preferred embodiment shown in FIG. 1, the elastic members 42 are affixed to the topsheet 55 and the backsheet 50 along the attachment areas 46 and left unaffixed from the topsheet 55 and the backsheet 50 along the free areas 48. The elastic members 42 may be affixed to the topsheet 55 and the backsheet 50 by attachment means (not shown) which are well known in the art. The attachment means may be, for example, a uniform continuous layer of adhesive, a patterned layer of adhesive or an array of separate lines or spots of adhesive. Alternatively, the elastic members 42 may be ultrasonically bonded or heat/pressure sealed into the topsheet 55 and/or the backsheet 50 using a variety of bonding patterns.

The fastening means 44 are joined to the elastic members 42, which in the preferred embodiment shown in FIG. 1 are positioned between the topsheet 55 and the backsheet 50. Therefore, in order for the fastening means 44 to extend beyond the longitudinal edges 25, the topsheet 55 and the backsheet 50 must be left unaffixed along portions of the longitudinal edges 25 through which portions the fastening means 44 can extend. Therefore, in the preferred embodiment shown in FIG. 1, the topsheet 55 and the backsheet 50 are affixed together along the length of the longitudinal edges 25 of the diaper 20 except along the portions of the longitudinal edges 25 which generally correspond to the free areas 48, whereat the topsheet 55 and the backsheet 50 are left unaffixed. One or more fastening means 44 are joined to the elastic members 42 in the free areas 48. Thus, during use, as shown in FIG. 2, the elastic members 42 are laterally displaceable in the free areas 48, thereby providing the fastening means 44 with the characteristic of being laterally displaceable.

One elastic member 42 which has been found to be suitable is an elastic strand having a cross section of 0.18 mm by 13.0 mm and made from natural rubber as available from East Hampton Rubber Thread Company of Stewart, Va., under the trademark L-1900 Rubber Compound. Other suitable elastic members 42 can be made from natural rubber, such as the elastic tape sold under the trademark Fulflex 9411 by Fulflex Company of Middletown, R.I. The elastic members 42 may also comprise any heat shrinkable elastic material as is well known in the art. Other suitable elastic members 42 comprise a wide variety of materials as are well known in the art including elastomeric films, polyurethane films, elastomeric foams, and formed elastic scrim.

Further, the elastic members 42 may take a multitude of configurations. For example, the width of the elastic members 42 may be varied from about 0.25 millimeters (0.01 inches) to about 25.0 millimeters (1.0 inch) or more; the elastic members 42 may have a rectangular, square, circular, etc., cross-section; the elastic members 42 may comprise a single strand of elastic material or may comprise several parallel or non-parallel strands of elastic material; or the elastic members 42 may be rectilinear or curvilinear.

The fastening means 44 may be any of those well known in the art, such as the fastening tape disclosed in U.S. Pat. No. 3,848,594, entitled "Tape Fastening System For Disposable Diaper", which issued to K. B. Buell on Nov. 19, 1974, and which patent is incorporated herein by reference. Alternatively, the fastening means 44 may be adhesively coated tapes which are looped around the elastic members 42 and secured to themselves, leaving at least a part of the adhesive part of the tape exposed beyond the longitudinal edge 25 of the diaper 20. Also, alternatively, the fastening means 44 may be velcro or velcro-like fasteners, buttons, snaps, hooks, ties, belts, and others.

In a particularly preferred embodiment of the present invention, the diaper 20 has a pair of side flaps 70, one or more side flap elastic members 74 associated with each of said side flaps 70, and a pair of gasketing cuffs 72. The side flaps 70 comprise those portions of the diaper 20 between the core side edges 67 and the longitudinal edges 25. The side flap elastic members 74 are operatively associated with the side flaps 70 so that they effectively contract or gather the side flaps 70 to provide gasketing cuffs 72 about the legs of the wearer. While the topsheet 55, the absorbent core 60, the backsheet 50, the side flaps 70, the side flap elastic members 74, and the gasketing cuffs 72 may be assembled in a variety of well known configurations, a preferred diaper configuration is described generally in U.S. Pat. No. 3,860,003, entitled "Contractable Side Portions For Disposable Diaper", which issued to K. B. Buell on Jan. 14, 1975, and which patent is incorporated herein by reference. In addition, a method and apparatus suitable for manufacturing a disposable diaper having elastically contractible gasketing cuffs are described in U.S. Pat. No. 4,081,301, entitled "Method and Apparatus for Continuously Attaching Discrete, Stretched Elastic Strands to Predetermined Isolated Portions of Disposable Absorbent Products" which issued to K. B. Buell on Mar. 28, 1979, and which patent is incorporated herein by reference.

The chassis means 15 can also be divided into regions. The chassis means 15 has front and back waist regions 30 and 32, respectively, each extending from the end edges 26 toward the lateral centerline 95 of the chassis means 15 a distance of from about ¼ to about ⅓ the length of the absorbent core 60. The waist regions comprise those portions of the chassis means 15 which, when worn, encircle the waist of the wearer. The chassis means 15 also has a crotch region 34. The crotch region 34 is that portion of the chassis means 15 between the waist regions 30 and 32, and comprises the portion of the chassis means 15 which, when worn, is positioned between the legs of the wearer and covers the lower torso of the wearer.

In use, the diaper 20 is positioned between the wearer's legs so that the crotch region 34 covers the lower torso, the front waist region 30 is positioned adjcent to the front waist area of the wearer and covers the front waist, and the back waist region 32 is positioned adjacent to the back waist area of the wearer and covers the back waist. The fastening means 44, which are preferably located in the rear waist portion 32, are then pulled about the waist of the wearer until the desired snugness is obtained at which time they are preferably associated with the back surface 54 of the backsheet 50, preferably in the front waist portion 30.

Figure 3:
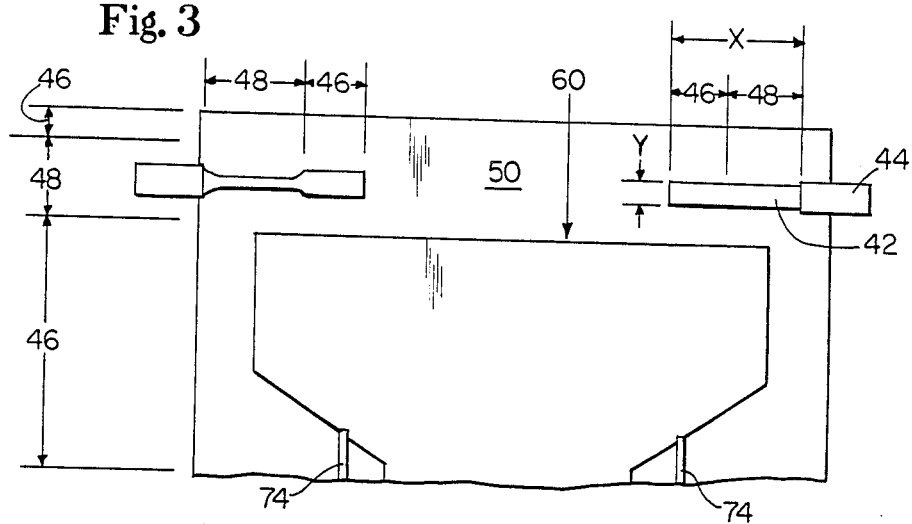
FIG. 3 is a partial plan view of an alternatively preferred disposable diaper embodiment of the present invention with the topsheet cut away.

As would be obvious to a person of ordinary skill in the art, the diaper 20 may take the form of a number of alternative embodiments. An alternatively preferred embodiment of the diaper 20 is shown in FIG. 3. In this embodiment, each elastic member 42 is laterally positioned. The fastening system 40 on the right side of FIG. 3 appears as it would at rest, while the fastening system on the left side of FIG. 3 appears as it might during use. A portion of each elastic member 42 is affixed to the topsheet 55 and the backsheet 50 in a fixed relation, along an attachment area 46. The free area 48 of each elastic member 42 remains free so that it can be laterally displaced. A fastening means 44, such as a fastening tape, is attached to the free area 48 of each elastic member 42, thereby providing each fastening means 44 with the characteristic of being laterally displaceable. As in FIG. 1, each elastic member 42 is positioned between the topsheet 55 and the backsheet 50, the topsheet 55 and backsheet 50 being left unaffixed along portions of the longitudinal edges 25 through which the fastening means 44 extend. Alternatively, the fastening systems 40 may be positioned adjacent the top surface 53 or adjacent the back surface 54 of the diaper 20.

Alternatively, the elastic member 42 may be an elastic strip which extends across or nearly across the width of the chassis means 15 and to each end of which are attached the fastening means 44.

Figure 4:
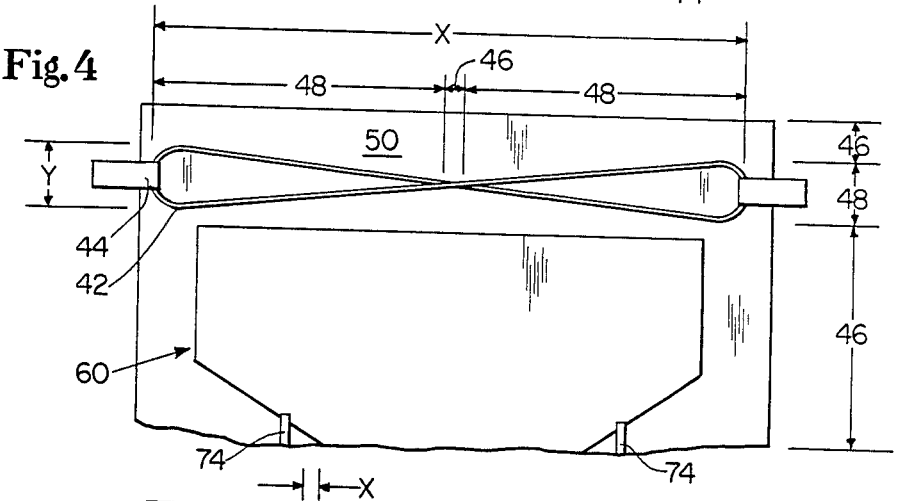
FIG. 4 is a partial plan view of an another alternatively preferred disposable diaper embodiment of the present invention with the topsheet cut away.
Figure 5:
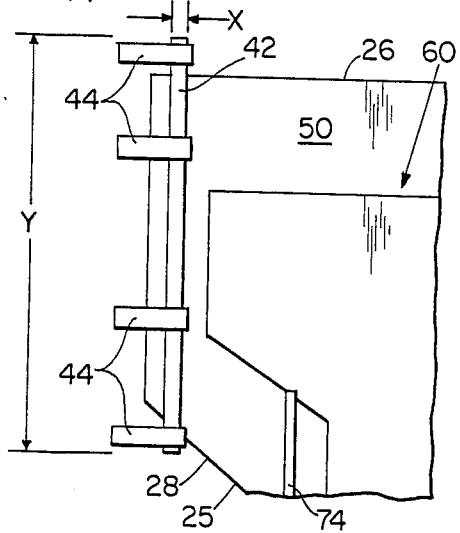
FIG. 5 is a partial plan view of yet another alternatively preferred disposable diaper embodiment of the present invention with the topsheet cut away.

Also, alternatively, the elastic member 42 may be a looped elastic band as shown in FIG. 4, to which fastening means 44 are attached.

A partial plan view of an alternatively preferred embodiment of the diaper 20 is shown in FIG. 5. In this embodiment, the elastic member 42 extends beyond the end edge 26 and the longitudinal edge 25. Fastening means 44 are joined to the elastic member 42 both within the periphery 28 and beyond the periphery 28.

While particular embodiments of the present invention have been illustrated and described, it would be obvious to those skilled in the art that various other changes and modifications can be made without departing from the spirit and scope of the invention.

What is claimed is:

1. An integral disposable absorbent garment having a longitudinal axis and a lateral direction orthogonal to the longitudinal axis, said garment comprising:
   a. a chassis means for absorbing and containing body exudates, said chassis means having a front waist region and a back waist region, said front waist region and said back waist region being generally oppositely disposed on said longitudinal axis;
   b. an elongate laterally displaceable elastic member, generally longitudinally positioned and having two ends affixed to said chassis means, said elongate member further having an unaffixed free area intermediate said affixed ends; and
   c. a fastening means joined to said unaffixed free area of said elastic member such that said fastening means is laterally displaceable.

2. The integral disposable absorbent garment as claimed in claim 1, wherein said chassis means comprises:
   a. a liquid permeable topsheet;
   b. a liquid permeable backsheet affixed to said topsheet; and
   c. an absorbent core positioned between said topsheet and said backsheet.

3. The integral disposable absorbent garment as claimed in claim 2, wherein said elastic member is longitudinally positioned in one of said waist regions.

4. The integral disposable absorbent garment as claimed in claim 3, wherein said elastic member is an elastic strand.

5. The integral disposable absorbent garment as claimed in claim 4, wherein said elastic member does not extend across the lateral dimension of said garment.

6. The integral disposable absorbent garment as claimed in claim 5, wherein said elastic member is positioned between said topsheet and said backsheet.

7. The integral disposable absorbent garment as claimed in claim 6, further comprising a longitudinal edge, wherein said topsheet and said backsheet are not affixed to each other along a portion of said longitudinal edge, through which portion said fastening means extend.

8. The integral disposable absorbent garment as claimed in claim 1, wherein a portion of said elongate member is affixed to said chassis means intermediate said affixed ends and further comprising a second fastening means joined to said second unaffixed area of said elongate member, whereby one said fastening means is disposed between the said affixed end and said intermediate affixed portion of said elongate member, and the other said fastening means is disposed between the other said affixed end and said intermediate affixed portion of said elongate member.

* * * * *

UNITED STATES PATENT AND TRADEMARK OFFICE
CERTIFICATE OF CORRECTION

PATENT NO. : 4,826,499

DATED : May 2, 1989

INVENTOR(S) : Nicholas A. Ahr

It is certified that error appears in the above-identified patent and that said Letters Patent is hereby corrected as shown below:

On the cover, Attorney, "Frederick" should be --Fredrick--.

Column 1, line 31, "as" should be --a--.

Column 1, line 32, "," (comma) should be --.-- (period).

Column 1, line 38, "4,006,081" should be --4,066,081--.

Column 3, line 39, "configuration" should be --configurations--.

Column 4, line 12, "top sheet" should be --topsheet--.

Column 4, line 18, "non-irrating" should be --non-irritating--.

Column 4, line 67, after "equivalent" insert --materials or combination of materials. The total absorbent capacity--.

Column 5, line 25, "be" should be --have--.

Column 5, line 68, "m" should be --mm--.

Column 6, line 32, "elasitc" should be --elastic--.

Column 6, lines 48 - 49, "lower most" should be --lowermost--.

Column 8, line 27, after "Products" insert --,-- (comma).

UNITED STATES PATENT AND TRADEMARK OFFICE
CERTIFICATE OF CORRECTION

PATENT NO. : 4,826,499

DATED : May 2, 1989

INVENTOR(S) : Nicholas A. Ahr

It is certified that error appears in the above-identified patent and that said Letters Patent is hereby corrected as shown below:

Column 10, line 10, "permeable" should be --impermeable--.

Column 10, line 35, after "ends" insert --so as to define a second unaffixed free area of said elongate member,--.

Signed and Sealed this

Twenty-seventh Day of February, 1990

*Attest:*

JEFFREY M. SAMUELS

*Attesting Officer*   *Acting Commissioner of Patents and Trademarks*